United States Patent [19]

Szijjártó née Auber et al.:

[11] Patent Number: 4,466,961

[45] Aug. 21, 1984

[54] COMPOSITION FOR THE TREATMENT OF EPITHELIAL INJURIES AND PROCESS FOR THE PREPARATION THEREOF

[75] Inventors: Emilia Szijjártó née Auber; Magda Ràskai, both of Budapest, Hungary

[73] Assignee: Humán Oltóanyagtermelö és Kutató Intézet, Gödöllo, Hungary

[21] Appl. No.: 358,874

[22] Filed: Mar. 16, 1982

[30] Foreign Application Priority Data

Mar. 17, 1981 [HU] Hungary ..................... 663/81

[51] Int. Cl.³ ............... A61K 31/70; A61K 31/335; A61K 31/235; A61K 31/23
[52] U.S. Cl. .................... 424/180; 424/279; 424/308; 424/312; 424/343
[58] Field of Search ........... 424/144, 308, 312, 180, 424/340, DIG. 13, 279

[56] References Cited

U.S. PATENT DOCUMENTS 3,833,732 9/1974 Saeed et al. .......... 424/DIG. 13
3,943,248 3/1976 Shulman ................. 424/196
4,235,889 11/1980 Evers ..................... 424/195

OTHER PUBLICATIONS

Handbook of Nonprescription Drugs, 6th Ed., p. 342, 1979.
Am J. Phar., Feb. 1942, pp. 62-63.
Manufacturing Chemist, 1942, p. 112.

*Primary Examiner*—Stanley J. Friedman
*Assistant Examiner*—John Rollins
*Attorney, Agent, or Firm*—Karl F. Ross; Herbert Dubno

[57] ABSTRACT

A new pharmaceutical composition suitable for the treatment of injuries to the skin, particularly burns, a process for the preparation thereof and a method of treatment for skin injuries is disclosed. The new composition relieves pain and promotes healing and is locally administered to the injury. The composition contains 5 to 20 mg of a tannic material, 5 to 15 mg of a carbohydrate, 0.5 to 6 mg of an anthocyane and/or a flavonone compound and/or pectin, 0.5 to 6 mg of plant wax, and 0.01 to 0.1 mg of volatile oil, balance a $C_2$ to $C_4$ alkanol, to yield 100 ml of composition.

4 Claims, No Drawings

COMPOSITION FOR THE TREATMENT OF EPITHELIAL INJURIES AND PROCESS FOR THE PREPARATION THEREOF

The object of our invention is a composition suitable for the treatment of injuries of the epithelium, furthermore its preparation and use.

Several kinds of methods have been known for the treatment of injuries of the epithelium, first of all burns. The accompanying symptoms of injuries depend on the seriousness of injuries and are selected from hyperaesthesia, pain, rubedo, edema, in more serious cases bulla formation and in the most serious case the damage of subcutaneous tissues, plasma flow, increased edema.

The first stage of provision of injuries optionally includes cooling of the skin surface, removal of shock, assuaging of pain, wound toilet (removal of the unnecessary pieces of epithelium, cutting of bullas, washing) and prophylaxis against infection.

The so called "air-dressing" as one of the well-known procedures of wound-toilet can only be used in a special environment which is low in germs (oxygen tent). For this reason the closed, bandaging treatment is widely popular.

There are transitory forms of treatment between the air-dressing and closed treatment as e.g. the so called "tannic" treatment which reduces exudation, has a pain assuaging effect, furthermore it binds the pathological decomposition products of protein (tannin).

A special variety of the open treatment is the use of film binding gels. A clear, impermeable layer is formed on the surface of the wound by the film binding gels and the following plasma.

The applied gels are based on plastics e.g. (polyvinyl derivatives, such as vulnoplastin, aeroplast). They are not suggested to be used in the case of serious burns of third degree because of anaerobic danger.

Preferred medicines of wound-treatment are the aerosol packed liquids, powders, ointments. Besides the above mentioned disinfecting washes a 2% mercurochrome solution can successfully be applied even if it is completed with silver nitrate and tannin.

The air-dressing of wounds in the case of deep burns is a disadvantage from the point of view that the spontaneous demarcation of the wound is delayed and so surgical intervention is delayed as well.

In curing serious burns good results were achieved by using lyophilized pig skin as a biological bandage or by the application of synthetic skin covering compositions (e.g. epigard).

During closed treatment the wound is protected from secondary infections by a sterile bandage.

Wounds are treated after a suitable toilet with a chemotherapeutic, antibiotic agent or an ointment.

The bandage can be a simple dry one. Instead of inert material a nylon thread tulle woven binding material is often used. Bandages impregnated with some other kind of material are often used as well. The most important view-point when closing these materials is that the bandage should not stick into the wound (paraffin, bee's wax etc.). A special form of hydrotherapeutics is when the bandage is washed from the wound in different baths.

(Artz, C. P., Reiss, E., Saunders W. B.: Treatment of Burns, Company (1957); János, Gy., Novák, J.: Égési sérülések (Burns), Bpl (1967); Jakab, Lencz, Forgács: Intenziv betegellátás (Intensiv medical attendance), Budapest (1957); Lynch, J. B., Lewis, S. R.: Symposium on the treatment of burns, Saint Louis (1973); and J. of Traum 13, 374–383 (1979).)

The disadvantage of bandage treatments is that covering a wound is accomplished by pain, and when the bandage is to be removed, it usually sticks to the wound, it does not close perfectly which involves danger of infection as well. In the case of a more tightly closing wound cover the problem of airing and continuous flowing away of discharge is not solved.

Another subject of the invention is a process for the preparation of a composition which is suitable for the treatment and post-treatment of surface wounds of the skin, first of all burns, surgical wounds, for post-treatment of frozen skin surface, further for epithelization in the case of wounds caused by abrasions or by caustic materials, by dissolving 5–20 mg tan material, 5–15 mg carbohydrate, 0.5–6 mg anthocyane and/or flavonone type compound and/or pectin, 0.5–6 mg plant wax, 0.01–0.1 mg volatile oils in alcohol containing 2–4 carbon atoms, preferably in ethanol and 100 ml. of a solution is obtained.

The object of our invention is the above preparation as well.

Pyrocatechol, tannic acid, gallic acid, digallic acid, pentadigalloyl-glucose can favorably be used as tan materials in the composition.

Glucose and/or fructose and/or xylose can be used as carbohydrate.

Quercetine and derivatives thereof can favorably be used as flavonone.

According to the invention anthocyane active ingredient and/or cyanidine can preferably be used as anthocyanin type compound. Derivatives of these compounds can also be used.

Volatile oils are very important components of the composition. For this purpose the following materials may be used: 40–90% geraniol and/or 4–15% nerol and/or 10–15% citronelol, eugenol, linanol, respectively the corresponding aldehydes.

The above listed components are indispensable in the composition as they ensure the disinfection of surface of the wound, cover it and increase epithelization and thus relieve pain.

It is preferred, however, if the activity of the composition is increased by further additives. It is advantageous if vitamins as additives are admixed to the preparation. For this purpose the following vitamins can be added: e.g. $A_1$, $B_1$, $B_6$, $B_{12}$, C, K, P.

Inorganic salts as further additives can also be admixed to the composition. Phosphates, chlorides and trace elements can preferably be added at traces, such as manganese, magnesium, calcium, cobalt, iron and zinc ions.

Plant hormones (e.g. auxines, kinetine) and enzymes with oxidative effect (e.g. peroxidase, catalase) can also be added as additives.

Each component can be dissolved simultaneously in ethanol if the components are soluble in ethanol. The components are preferably dissolved first in each other then in some water and then dissolve them in the composition. Optionally a solution transmitter can be used as well (e.g. ether). Vitamins A and K are preferably added to the system dissolved in volatile oils. Vitamin C is added in the form of a concentrated aqueous solution.

The components are preferably dissolved at 0°–30° C., preferably at a lower temperature than room temperature. Stock solutions are preferably prepared—possibly in ethanol or water—and when preparing the final solution the components are taken in exact amounts from this stock solution. The stock solutions are kept at a cool place until they are mixed together.

The ethanol solution containing the main components is very stable and can be stored for a long time at room temperature, protected from sunshine.

The composition according to the invention is to be applied on the surface of the wound after washing the surface, optionally cooling with plenty of water, washing and neutralizing in case of caustic materials in the form of a finely divided thin layer. The composition is preferably applied on the skin or on the surface of the wound by painting, bathing, particularly by spraying.

The above treatment is repeated until constant pain ceases. This treatment can be repeated several times. The surface of the wound should be kept away from water, soap during the treatment.

As a result of this treatment a film with tiny, thin vacuoles can be observed over the surface of the wound which protects the wound from infection while the active ingredients of the composition act as epitheliogenic, disinfectant, analgesic agents.

Each component can directly be transsolved from plant extracts into the composition or the extracts can be added to the composition.

The composition according to the invention can be finished as spray or as a solution with which the surface of the wound can be dressed, painted or bathed, if desired inert additives (e.g. carrier gas) can be added as well.

The details of our procedure will be illustrated by the following Examples.

EXAMPLE 1

The following stock solution is prepared:

Solution I 1000 ml 96% ethanolic (PhHgVI) tincture, which contains:
10 g gallic acid
5 g pyrocatechol
0.5 g anthocyanine
0.2 mg auxine
0.15 mg kinetine

Solution II 15 g glucose (PhPgVI)
3 mg vitamin C (acidum ascorbinicum) (PhHgVI)
20 mg vitamin $B_1$ (anaerinum hydrochloricum) (PhHgVI)
20 mg vitamin $B_6$ (pyridoxinum hydrochloricum) (PhHgVI)
10 mg vitamin $B_{12}$ (cyanocobalaminum) (PhHgVI)
ad 1000 ml 25% ethyl alcohol

Solution III 4 g cere alba
25 mg geraniol
7 mg nerol
15 mg citronelol
3 mg eugenol
1 mg carotene
ad 1000 ml 25% ethylether (PhHgVI).

The stock solutions are mixed as follows:
10 ml solution I
10 ml solution II
10 ml solution III
ad 1000 ml 96% ethyl alcohol (PhHgVI)

The solution is filtered through an alcohol-resistant diaphragm and is filled in spray bottles.

EXAMPLE 2

The following stock solutions are prepared:
Solution I is a 1000 ml 96 and ethyl alcoholic (PhHgVI) tincture which contains
5 g digallic acid
0.8 g anthocyanine
2.6 g cyanidine
15 g cyanidine
0.15 mg auxine
0.1 mg kinetine.

Solution II 10 g glucose (PhHgVI)
5 g rhamnose (PhHgVI)
20 mg vitamin C (acidum ascorbinicum) (PhHgVI)
3 mg vitamin P (rutin)
0.2 mg peroxidase
ad 1000 ml distilled water.

Solution III 2 mg vitamin A (axerophthalum) (PhHgVI)
70 mg geraniol
4 mg nerol
20 mg citronelol
3 mg eugenol
3 mg linalool
2 mg cera flava
4 mg cera alba
ad 1000 ml ethyl ether (ether ad narcosum) PhHgVI

Solution IV 20 mg vitamin $B_1$ (aneurinum hydrochloricum) (PhHgVI)
15 mg vitamin $B_6$ (pyridoxinum hydrochloricum) (PhHgVI)
5 mg $B_{12}$ vitamin (cyanocobalaminum) (PhHgVI)
ad 1000 ml 25% ethyl alcohol (PhHgVI)

The stock solutions are mixed as follows:
10 ml solution I
10 ml solution II
10 ml solution III
10 ml solution IV
ad 1000 ml 96% ethyl alcohol (PhHgVI)

The solution is filtered through an alcohol-resistant diaphragm and is filled in spray bottles.

EXAMPLE 3

The following materials are mixed together:
10 mg gallic acid
5 mg pyrocatechol
15 mg glucose
0.5 mg anthocyanine
4 mg cera alba (dissolved in ether)
0.05 mg in ether dissolved volatile oils containing:
  50% geraniol
  15% nerol
  30% citronelol
  5% eugenol
0.003 mg vitamin C
0.05 mg vitamin B ($B_1$, $B_6$, $B_{12}$ in aā dose)
and then dissolved in 96% sterile ethanol so as to obtain 100 ml solution. The solution is filtered sterile and is filled in spray bottles.

EXAMPLE 4

The following materials are mixed together:
15 mg gallic acid
5 mg digallic acid
0.8 mg anthocyanine
2.6 mg cyanidine
10 mg glucose
5 mg rhamnose
6.0 mg plant wax
0.1 mg volatile oils in ether containing:
  70% geraniol
  4% nerol
  10% citronelol
  3% eugenol
  3% linanool
0.03 mg vitamin C
0.04 mg vitamin B
0.02 mg vitamin A (which is to be introduced in an oil phase).

EXAMPLE 5

Determination of the dry substance

The dry substance of the solution examined according to par. 2.2. page 110 in volume I of PhHgVI shall not be less than 0.03%.

EXAMPLE 6

Determination of sugar in a colorimetric way (antron)

(Literature: R. L. Whistler, W. L. Wolfrom: "Methods in Carbohydrate Chemistry, I.," Academic Press, New York, 1962).

The total sugar content in the solution is 40 to 50% of the dry substance.

EXAMPLE 7

Determination of tan substances colorimetrically according to Mattil and Filter (Literature: Kakác-Vejdelek: "Handbuch der Kolorimetrie II.," Vg. Fischer Verlag, Jena, 1963).

The bark substance in the solution is about 20% of the dry substance.

EXAMPLE 8

Qualitative requirements of the solution of therapeutic concentration

The solution is to be pale yellowish pink, transparent, crystal-clear and without any sediment.
1. Testing of coloring agents:
   5 ml of the solution was tested according to paragraph 1.1, page 102 volume I of PhHgVI. The color of the solutions should be between the color grades 3-5.
2. Testing of acidity, alkalinity:
   The pH value of the freshly boiled and cooled solution diluted with distilled water at a ratio of 1:9 shall range from 5.00 to 6.00 measured with an electric pH-meter.
3. Density
   When measuring at 20° C., the value shall range from 0.804 to 0.806.

EXAMPLE 9

Acute toxicity tests

Up to 200 ml of solution is necessary for a single treatment of a burn wound extending up to 50% of the body surface of an adult with a body weight of 60 kg. Supposing three treatments a day, an adult with serious burns can be treated with 600 ml of solution. The total dry substance of this volume of solution amounts to 200 mg and converted into body weight, this corresponds to 200:60=3.0 mg dry substance per kg.

In rabbit and mice toxicity tests the following doses were applied:

The tests were carried out with the residue of the evaporated solution redissolved in the aqueous solution of sodium hydrogen carbonate (pH=8.2) sterilized by filtration. The dosage was determined according to the dry substance. The test results are shown in the following table:

| Animal species | Number | Method of inoculation | Dosage mg/kg | Human dosage per kg × factor | Time of observation | Reaction |
|---|---|---|---|---|---|---|
| Mice | 12 | i.p. | 38.5 | 13 × | 2 months | none |
| Mice | 12 | i.p. | 77.0 | 26 × | 2 months | 2 + 2 2nd and 3rd day |
| Rabbits | 12 | i.v. | 8.0 | 2.7 × | 2 week to 2 months | none |
| Rabbits | 5 | i.v. | 20.0 | 6.7 × | 2 weeks to 2 months | none |
| Rabbits | 5 | i.v. | 100.0 | 33 × | 2 weeks to 2 months | |

The weight of mice was about 20 g, and the weight of rabbits was about 2.5 to 3.5 kg.

The above data show that not even a 30-times higher dosage than the human dosage applied to the skin is toxic to the rabbit.

EXAMPLE 10

Burns caused by glowing metal

The hair was removed by shaving the entire back of rabbits and they were anaesthetized. A metal plate with a surface of 6 cm² was heated by gas flame to the glow and second-degree, respectively third-degree burns were caused by burning the skin for 2 to 5, respectively 2×5 seconds.

After burning the skin was cooled by cold water, by washing, a treatment with the composition followed 15 to 20 minutes later consisting of two sprayings. This treatment was repeated 4-5 hours later.

Further treatments were applied twice a day until the crusts started to peel off, then once a day, and later every second day. The crusts were removed by scissors. As control the following treatments were used: petrolatum, oxycort spray, alcoholic panthenol solution, mercurochromium solution, silver-nitrate solution.
Total burnt surface:
121 pieces treated with composition
110 pieces control.

In the course of treatments it could be observed that on the burnt surface and its surroundings neither adema nor inflammation were observed. Hard crusts developed on the burnt surface on the second or third day after burning which started to peel off between 8-10 days at the edges and under the crust a perfectly healthy epithelium could be observed.

The full peeling of crusts could be observed 15–25 days after burning (according to the grade of burning) but in each case sound epithelium was to be observed under the peeled off crusts. Subsequently the growth of hair starts.

On the control surfaces edema and inflammation could be observed and peeling off took place 6–8 days later. Under the peeled off crusts often non-epithelized spots could be seen which delayed the perfect healing by another 8–10 days. The growth of hair started also later and in some cases it did not start at all.

The time of healing is summed up in the following table:

| Number of burnt areas | Method of treatment | Healing time in days |
| --- | --- | --- |
| 121 nr. 1–4 | composition | 15 to 30 |
| 24 | 0.5% silver nitrate | 15 to 26 |
| 23 | 2% mercurochromium | 25 to 32 |
| 24+ | Oxycort | 28 to 60 |
| 5 | Panthenol | could not be evaluated because the animals died off |
| 32 | 95% ethyl alcohol | 23 to 40 |
| 2 | boric acid ointment | 36 to 40 |

+Not more than 15 burnt areas could be evaluated because of animals dying off.

The time of healing was closely related to the time of burning.

EXAMPLE 11

Microscopic checking of the film formation on the skin surface

The natural color agents of the solution of the therapeutic concentration are insufficient for making the vacuoles visible under the microscope. Acid fuchsin staining must therefore be applied. Approximately 0.05 g of crystalline coloring agent is dissolved in approximately 20 ml of the composition and the solution is subsequently filtered through analytical filter paper and finally sterile filtration is used. The sterile filtered extract is dropped on the defatted slide by capillary and evaporated to dryness. This operation is repeated several times and the slide is finally tested under the microscope at a magnification of 1000×. Vacuoles are equally distributed in the film.

EXAMPLE 12

Determination of bacteriostatic activity

The evaporated residue of dry substance of the composition was redissolved in a 1% solution of sodium hydrogen carbonate and was sterilized by filtration. From this above alcoholfree solution an amount was given to the buillon medium corresponding to 5 mg/ml final concentration. This medium was vaccinated from the 37° C., liquid 24-hour-culture of various bacterial strains. The growth of bacteria was read off 24 hours later.

Our results are summed up in the following table:

| bacterial strain | growth | control culture |
| --- | --- | --- |
| Staphylococcus aureus 112001 | none | normal growth |
| Staphylococcus aureus 112002 | " | " |
| Staphylococcus aureus 306 | " | " |
| Staphylococcus aureus 211 | " | " |
| Staphylococcus aureus 223 | " | " |
| Staphylococcus aureus Woos 46 | " | " |
| Bacillus subtilis | normal growth | " |
| Proteus vulgaris 61370 | " | " |
| Pyocyaneus aeruginosa 170014 | " | " |

On testing this alcoholic solution, the same bacterial strains and same methods were used as described in the previous paragraph.

Our results correspond to the ones described in the previous paragraph.

EXAMPLE 13

When burnt spots were irritated mechanically, in the case of pain (e.g. pushing), animals reacted by jerking of the skin, change in behavior, eventually tone effect.

Besides, their general behavior (movement, nourishment) can also be evaluated. Animals remained indifferent when their burnt spots treated with our composition were touched, but control animals reacted on touching as described above and their reaction to moving was a sound of pain. When several burnt spots were treated with control medicines animals did not take nourishment at all and their body weight reduced. Burns with a surface of 6—6 cm$^2$ were caused on 12 places on the shaved skin of some of these animals and they were treated with our compoisition. Animals took nourishment and their body weight developed normally as well.

As test animals rabbits weighing 2.5 to 3.5 kg were used.

EXAMPLE 14

30% of the shaved back area of the rabbits was burnt by 100° C. hot water. The animal treated with our composition was perfectly cured within 4 weeks and its hair grew perfectly as well. In case of the other animal treated with alcohol there is a excoriation of the size of a child's palm even after 3.5 months' time treatment.

EXAMPLE 15

Owing to the negative nitrogen balance and intake of food determined by the general state of the animal during this illness (intake of food is in close connection with pain sense), the therapeutical effect can be well demonstrated by a body weight curve. For this reason body weight was continuously registered during the time of healing in the case of animals burnt with a metal plate with a surface of 6 cm$^2$ on 8–10 spots.

The body weight of a rabbit treated exclusively with our composition steadily increased after burning. The total increase of its body weight until the 36th day was 950 g compared to the initial weight.

The rabbit treated exclusively with silver nitrate lost 200 g body weight in 13 days. It reached its initial weight on the 20th day. Subsequently, up to the 36th day after burning, its body weight increased by 200 g.

The rabbit treated exclusively with mercurochromium lost 600 g its body weight in 27 days. Its body weight increased but on the 36th day after burning, its weight was still less by 350 g than its initial body weight.

Rabbit treated with our composition on one side and silver nitrate on the other side lost 200 g of its body weight up to the third day after burning. It regained its initial body weight on the 9th day. On the 36th day after burning, its body weight increased by 650 g compared to the initial weight. A rabbit treated with our composition and simultaneously with ethyl alcohol lost 100 g body weight until the 3rd day after burning. It regained its initial weight on the 13th day. Its body weight increased by 600 g on the 36th day compared to its initial weight.

EXAMPLE 16

The following ingredients are used to prepare a composition of 1000 g:

| | |
|---|---|
| digalloyl-glucose | 5.25 g |
| penta-digalloyl-glucose | 3.00 g |
| gallic acid | 0.75 g |
| catechol tannic acid | 6.00 g |
| quercetine | 0.90 g |
| cempherol | 0.75 g |
| apigenine | 0.60 g |
| delphinine | 0.75 g |
| cyanine | 0.75 g |
| glucose | 3.75 g |
| fructose | 3.00 g |
| kitose | 0.30 g |
| xylose | 0.15 g |
| pectin (ultra-amilo-pectin) | 12.80 g |
| bee-wax | 3.75 g |
| carnauba wax | 3.75 g |
| geraniol | 0.0045 g |
| nerol | 0.0015 g |
| citronellol | 0.003 g |
| citral | 0.003 g |
| $FeCl_3$ | 0.0003 g |
| $MnCl_2$ | 0.0002 g |
| $CoCl_2$ | 0.0001 g |
| $MgCl_2$ | 0.0001 g |

The above ingredients are admixed and completed with 96% ethanol to give a total of 1000 g. The solution is filtered under sterile conditions and filled into bottles for use as a spray.

Some of the specific ingredients can also be obtained in groups from plants by way of extraction and can be added as such to the composition.

We claim:

1. A process for the preparation of a composition for the treatment and post treatment of burns, for the treatment of healing surgical wounds, or of frozen skin surface, and for promoting epithelization of wounds caused by abrasion or caustic materials which comprises the steps of:

dissolving 5 to 20 mg of a tannic compound selected from the group consisting of pyrocatechol, tannic acid, gallic acid, digallic acid, catechol tannic acid, and pentadigalloyl glucose, 5 to 15 mg of a carbohydrate selected from the group consisting of glucose, fructose and xylose, 0.5 to 6 mg of a compound selected from the group consisting of quercetine, apigenine, cyanidine, cyanine, delphinin, pectin, and mixtures thereof, 0.5 to 6 mg of a wax selected from the group consisting of carnauba wax and bee wax, and 0.01 to 0.1 mg of a volatile oil selected from the group consisting of geraniol, nerol, citronelol, eugenol, linalol, and corresponding aldehydes, or mixtures thereof, in a $C_2$–$C_4$ alkanol to obtain 100 ml of composition.

2. The process defined in claim 1 wherein the $C_2$–$C_4$ alkanol is ethanol present in a concentration of 70 to 100%.

3. A composition for the treatment of burns, for the treatment of healing surgical wounds, or frozen skin surface, and for promoting epithelization of wounds caused by abrasions or caustic materials which comprises:

5 to 20 mg of a tannic compound selected from the group consisting of pyrocatechol, tannic acid, gallic acid, digallic acid, catechol tannic acid, and pentadigalloyl glucose;

5 to 15 mg of a carbohydrate selected from the group consisting of glucose, fructose, and xylose;

0.5 to 6 mg of a compound selected from the group consisting of quercetine, apigenine, cyanidine, cyanine, delphinin, pectin, and mixtures thereof;

0.5 to 6 mg of a wax selected from the group consisting of Carnauba wax and bee wax; and 0.01 to 0.1 mg of a volatile oil selected from the group consisting of geraniol, nerol, critronelol, eugenol, linalol, and corresponding aldehydes, or mixtures thereof, per 100 ml of a 70 to 100% $C_2$–$C_4$ alkanol solution.

4. A method for the treatment of burns, for the treatment of healing surgical wounds, or frozen skin surface, and for promoting epithelization of wounds caused by abrasion or caustic materials which comprises the step of applying to the skin of a susceptible subject, a pharmaceutically effective amounts of the composition defined in claim 3.

* * * * *